(12) United States Patent
Roeder (10) Patent No.: US 11,096,810 B2
(45) Date of Patent: Aug. 24, 2021

(54) PRELOADED PUSHER TIP FOR ENDOGRAFTS

(71) Applicant: Cook Medical Technologies LLC, Bloomington, IN (US)

(72) Inventor: Blayne A. Roeder, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 359 days.

(21) Appl. No.: 16/196,290

(22) Filed: Nov. 20, 2018

(65) Prior Publication Data

US 2019/0159915 A1 May 30, 2019

Related U.S. Application Data

(60) Provisional application No. 62/591,993, filed on Nov. 29, 2017.

(51) Int. Cl.
*A61F 2/95* (2013.01)
*A61M 29/00* (2006.01)
(Continued)

(52) U.S. Cl.
CPC ............... *A61F 2/95* (2013.01); *A61F 2/954* (2013.01); *A61F 2/966* (2013.01); *A61M 29/00* (2013.01); *A61F 2/07* (2013.01); *A61F 2002/061* (2013.01); *A61F 2002/8486* (2013.01); *A61F 2002/9511* (2013.01); *A61F 2002/9665* (2013.01); *A61M 25/0069* (2013.01)

(58) Field of Classification Search
CPC .. A61M 25/0069; A61M 25/09; A61M 29/00; A61F 2/95; A61F 2/954; A61F 2/962; A61F 2/966; A61F 2002/061; A61F 2002/9511; A61F 2002/9665
See application file for complete search history.

(56) References Cited

U.S. PATENT DOCUMENTS

| 4,631,059 A | 12/1986 | Wolvek et al. |
| 4,697,573 A | 10/1987 | Schiff |

(Continued)

FOREIGN PATENT DOCUMENTS

| AU | 2009200350 B1 | 7/2009 |
| EP | 2626045 A1 | 8/2013 |

(Continued)

OTHER PUBLICATIONS

European Search Report for EP Application No. 18208975.5 dated Aug. 16, 2019, 9 pages.

(Continued)

*Primary Examiner* — Robert A Lynch
(74) *Attorney, Agent, or Firm* — Crowell & Moring LLP (57) ABSTRACT

An endovascular prosthesis delivery system comprising: a guide wire catheter; a nose cone dilator at the proximal end of the guide wire catheter; and a pusher catheter comprising a lumen configured to receive the guide wire catheter therethrough and at least one longitudinal auxiliary lumens configured to receive an auxiliary catheter. The pusher catheter may have recess in the guide wire lumen. The recess may be configured to receive a portion of the nose cone dilator when the guide wire catheter is withdrawn distally.

20 Claims, 9 Drawing Sheets

(51) Int. Cl.
    *A61F 2/966*     (2013.01)
    *A61F 2/954*     (2013.01)
    *A61M 25/00*     (2006.01)
    *A61F 2/848*     (2013.01)
    *A61F 2/06*     (2013.01)
    *A61F 2/07*     (2013.01)

(56) References Cited

U.S. PATENT DOCUMENTS

| | | | |
|---|---|---|---|
| 4,794,928 | A | 1/1989 | Kletschka |
| 5,261,887 | A | 11/1993 | Walker |
| 5,693,083 | A | 12/1997 | Baker et al. |
| 5,769,885 | A | 6/1998 | Quiachon et al. |
| 6,350,287 | B1 | 2/2002 | Lenker et al. |
| 6,808,510 | B1 * | 10/2004 | DiFiore ............ A61M 25/0068 604/171 |
| 6,827,726 | B2 | 12/2004 | Parodi |
| 6,939,352 | B2 | 9/2005 | Buzzard et al. |
| 6,939,370 | B2 | 9/2005 | Hartley et al. |
| 7,413,573 | B2 | 8/2008 | Hartley et al. |
| 7,435,253 | B1 | 10/2008 | Hartley et al. |
| 7,611,529 | B2 | 11/2009 | Greenberg et al. |
| 7,678,141 | B2 | 3/2010 | Greenan et al. |
| 7,763,063 | B2 | 7/2010 | Arbefeuille et al. |
| 7,803,177 | B2 | 9/2010 | Hartley et al. |
| 7,814,662 | B2 | 10/2010 | O'Neal |
| 7,867,270 | B2 | 1/2011 | Hartley et al. |
| 7,892,275 | B2 | 2/2011 | Hartley et al. |
| 7,914,572 | B2 | 3/2011 | Hartley et al. |
| 8,012,193 | B2 | 9/2011 | Hartley et al. |
| 8,043,354 | B2 | 10/2011 | Greenberg et al. |
| 8,114,145 | B2 | 2/2012 | Hartley et al. |
| 8,118,854 | B2 | 2/2012 | Bowe |
| 8,709,061 | B2 | 4/2014 | Greenberg et al. |
| 8,753,385 | B2 | 6/2014 | Hartley et al. |
| 8,870,939 | B2 | 10/2014 | Roeder et al. |
| 8,876,879 | B2 | 11/2014 | Hartley et al. |
| 9,060,887 | B2 | 6/2015 | Hartley et al. |
| 9,504,555 | B2 | 11/2016 | Hartley et al. |
| 2001/0039388 | A1 | 11/2001 | Korotko et al. |
| 2002/0095204 | A1 | 7/2002 | Thompson et al. |
| 2002/0143383 | A1 | 10/2002 | Paroldi |
| 2002/0165554 | A1 | 11/2002 | Dworschak et al. |
| 2003/0105427 | A1 | 6/2003 | Lee et al. |
| 2003/0135259 | A1 | 7/2003 | Simso |
| 2003/0158597 | A1 | 8/2003 | Quiachon et al. |
| 2003/0181923 | A1 | 9/2003 | Vardi |
| 2004/0002754 | A1 | 1/2004 | McDermott |
| 2004/0049256 | A1 | 3/2004 | Yee |
| 2004/0097876 | A1 | 5/2004 | Shkolnik |
| 2004/0098079 | A1 | 5/2004 | Hartley et al. |
| 2004/0106974 | A1 | 6/2004 | Greenberg et al. |
| 2004/0148000 | A1 | 7/2004 | Bilge |
| 2004/0167618 | A1 | 8/2004 | Shaolian |
| 2004/0230287 | A1 | 11/2004 | Hartley et al. |
| 2005/0085842 | A1 | 4/2005 | Eversull et al. |
| 2005/0131518 | A1 | 6/2005 | Hartley et al. |
| 2006/0253088 | A1 * | 11/2006 | Chow ................ A61M 25/003 604/284 |
| 2007/0043425 | A1 | 2/2007 | Hartley et al. |
| 2007/0083215 | A1 | 4/2007 | Hamer et al. |
| 2007/0219614 | A1 | 9/2007 | Hartley |
| 2007/0219621 | A1 | 9/2007 | Hartley et al. |
| 2007/0233220 | A1 | 10/2007 | Greenan |
| 2007/0282419 | A1 | 12/2007 | Hilaire |
| 2007/0299499 | A1 | 12/2007 | Hartley et al. |
| 2008/0033354 | A1 | 2/2008 | Hartley et al. |
| 2008/0109065 | A1 | 5/2008 | Bowe |
| 2008/0319524 | A1 | 12/2008 | Yachia |
| 2009/0024137 | A1 | 1/2009 | Chuter et al. |
| 2009/0171434 | A1 | 7/2009 | Rusk et al. |
| 2009/0192518 | A1 | 7/2009 | Golden et al. |
| 2010/0198328 | A1 | 8/2010 | Hartley et al. |
| 2011/0054594 | A1 | 3/2011 | Mayberry |
| 2011/0144735 | A1 | 6/2011 | Hartley et al. |
| 2011/0282425 | A1 | 11/2011 | Dwork |
| 2011/0307048 | A1 | 12/2011 | Ivancev et al. |
| 2012/0172887 | A1 | 7/2012 | Hatfield |
| 2014/0121753 | A1 | 5/2014 | Dorn et al. |

FOREIGN PATENT DOCUMENTS

| | | |
|---|---|---|
| EP | 2745813 A1 | 6/2014 |
| JP | 2007-503923 | 3/2007 |
| WO | WO 01/67993 A2 | 9/2001 |
| WO | WO 03/101518 A1 | 12/2003 |
| WO | WO 2004/089249 A1 | 10/2004 |
| WO | WO 2007/059280 A1 | 5/2007 |
| WO | WO 2007/142962 A2 | 12/2007 |
| WO | WO 2008/042270 A1 | 4/2008 |
| WO | WO 2009/148602 A1 | 12/2009 |
| WO | WO 2011/159504 A1 | 12/2011 |
| WO | WO 2015/075708 A1 | 5/2015 |

OTHER PUBLICATIONS

Search Information Statement for corresponding Australian patent application No. AU 2010202487, dated Apr. 11, 2011, 4 pgs.
Examiner's report No. 2 for corresponding Australian application patent No. AU 2010202487, dated Jun. 15, 2011, 3 pgs.
Patent Examination Report No. 1 for Australian application patent No. AU 2011265608, dated Apr. 30, 2014, 4 pgs.
Examination Report for EP Application No. 11727368.0, dated Jul. 7, 2016, 5 pages.
Extended European Search Report for EP Application No. 152755270.5, dated May 2, 2016, 5 pgs.
Extended European Search Report for EP Application No. 17152719.5, dated Feb. 22, 2017, 6 pgs.
European Search Report for EP Application No. 17162386, dated Sep. 25, 2017, 9 pgs.
Examination Report for EP Application No. 17162386, dated Oct. 23, 2020, 6 pgs.
Extended European Search Report for EP Application No. 18275193.3, dated May 10, 2019, 7 pgs.
Office Action and English translation for JP Application No. 2011548010, dated Jul. 26, 2013, 4 pages.
Office Action and English translation for JP Application No. 2011548010, dated Dec. 20, 2013, 4 pages.
International Search Report and Written Opinion for PCT/US2007/012730, dated Nov. 28, 2007, 12 pages.
International Preliminary Report on Patentability and Written Opinion for PCT/US2007/012730, dated Dec. 3, 2008, 8 pages.
International Search Report and Written Opinion for PCT/US2007/016574, dated Mar. 6, 2008, 12 pages.
International Preliminary Report on Patentability and Written Opinion for PCT/US2007/016574, dated Feb. 5, 2009, 8 pages.
International Search Report and Written Opinion for PCT/US2010/020738, dated Apr. 21, 2010, 14 pgs.
International Search Report and Written Opinion for PCT/US2011/039241, dated Oct. 7, 2011, 12 pgs.
International Preliminary Report on Patentability and Written Opinion for PCT/US2011/039241, dated Dec. 19, 2012, 7 pgs.

* cited by examiner

PRELOADED PUSHER TIP FOR ENDOGRAFTS

TECHNICAL FIELD

This disclosure relates to a medical device. More particularly, it relates to apparatus and methods for deploying endoluminal prostheses in a body vessel, duct, or lumen.

BACKGROUND

Endoluminal prostheses may be inserted into a body lumen such as an anatomical vessel or duct for various purposes. Prostheses may maintain or restore patency in a formerly blocked or constricted passageway or they may be used for different procedures. For example, a prosthesis may include one or more stents placed in or about a graft, and the stents may hold the graft in an open configuration to treat an aneurysm. Additionally, stents coupled to one or both ends of a graft may extend proximally or distally away from the graft to engage a healthy portion of a vessel wall away from a diseased portion of an aneurysm to provide endovascular graft fixation.

In some cases a stent graft may include at least one fenestration to enable an extension leg or arm graft to be extended from a main stent graft in an internal lumen through the fenestration to allow the leg or arm graft to extend into a branch vessel of the lumen. Such a situation may exist in the aorta with renal arteries extending from the aorta. When there is an aneurysm in this region which includes the junction of the aorta with the renal arteries then it is desirable to not only have a main graft which spans the aneurysm but also extension legs or arms which extend from the main graft into the renal or other arteries.

SUMMARY

It is an object of the present application to provide a preloaded pusher tip for endografts with an improved visibility for the placement of bridging stents in one of more fenestrations of a stent graft.

According to a first aspect of the present invention, an endovascular prosthesis delivery system includes a slidable guide wire catheter having a proximal end; an elongate nose cone dilator secured to the proximal end of the guide wire catheter; a pusher catheter having a most proximal end and at least two lumens, one of which is a guide wire lumen and at least one which is an auxiliary lumen. The guide wire catheter is at least partially disposed in the pusher catheter lumen, and the pusher catheter has a proximal taper adjacent the proximal most end of the pusher catheter. The guide wire lumen proximally terminates in a guide wire lumen opening disposed in the taper, distal to the most proximal end of the pusher catheter. The at least one auxiliary lumen proximally terminates in an auxiliary lumen opening located closer to the most proximal end of the pusher catheter than the guide wire lumen opening. This allows for a retraction of the nose cone dilator farther in the distal direction than with known delivery systems.

The guide wire lumen may include a recess of a shape that at least partially conforms to the shape of the nose cone dilator to facilitate retraction of the nose cone dilator into the guide wire lumen.

Generally, the nose cone dilator may at least partially rest within the recess of the pusher catheter and at least partially extend distally of the most proximal end of the pusher catheter when in a retracted position. Thus, the nose cone dilator extends distally beyond the most proximal end of the pusher catheter when in a retracted position. For example, the nose cone dilator may have a retracted position, in which more than half of a length of the nose cone dilator is located distal from the most proximal end of the pusher catheter.

According to another aspect of the present invention, the taper may proximally end at an end face of the pusher catheter. The end face extends transverse to a longitudinal direction of the pusher catheter and transverse to the taper. The at least one auxiliary lumen opening may be located in the end face.

According to a further aspect, at least a distal taper of the nose cone dilator is disposed inside the guide wire lumen when the nose cone dilator is in a retracted position.

According to yet another aspect, the pusher endovascular prosthesis delivery system may additionally comprise a stent graft having one or more fenestrations, and the stent graft is connected to the proximal end of the pusher catheter when in a delivery configuration.

According to another aspect of the present invention, an endovascular prosthesis delivery system comprises a guide wire catheter having a guide wire lumen therethrough; a nose cone dilator at the proximal end of the guide wire catheter, the nose cone dilator comprising a distal end and a distally facing capsule on the distal end of the nose cone dilator; and a pusher catheter having a most proximal end. The pusher catheter includes a guide wire lumen configured to receive the guide wire catheter therethrough and at least one longitudinal auxiliary lumens configured to receive an auxiliary catheter. The guide wire catheter extends through the pusher lumen, and the guide wire catheter is able to move longitudinally and rotationally with respect to the pusher catheter. The pusher catheter has a recess in the guide wire lumen adapted to a shape of the nose cone dilator.

According to a further aspect, a catheter device comprises a tubular body that extends from a proximal end to a distal end; an auxiliary lumen extending along the length of the tubular body that is configured to receive an auxiliary catheter, the auxiliary lumen having a proximal opening; and a guide wire lumen extending along the length of the tubular body, the guide wire lumen being configured to receive a guide wire catheter. The guide wire lumen has a proximal opening disposed distal to the proximal opening of the auxiliary lumen catheter.

The proximal end of the tubular body may have a one-sided taper in an oblique direction relative to a longitudinal direction of the catheter device. The taper proximally may end at an end face of the pusher catheter, wherein the end face extends transverse to a longitudinal direction of the pusher catheter and transverse to the taper.

The auxiliary lumen may proximally terminate in the end face.

According to another aspect, the guide wire lumen opening may be configured to receive a distal end of a nose cone dilator. For example, the guide wire lumen opening may be configured to receive a distal portion of the nose cone dilator to place more than half of a length of the nose cone dilator distal of the proximal end of the pusher catheter. For this purpose, the guide wire lumen may include a recess with a shape adapted to the nose cone dilator for placing a distal portion of the nose cone dilator inside the guide wire lumen.

The guide wire lumen opening may be between 10-50 mm distal to the proximal end of the catheter.

Further details and benefits become apparent from the following description of preferred embodiments shown in the attached drawings.

DETAILED DESCRIPTION

The drawings are provided herewith for purely illustrative purposes and are not intended to limit the scope of the present invention.

In the present application, the term "proximal" when referring to a delivery device refers to a direction that is farthest away from the operator using a delivery device, while the term "distal" refers to a direction that is generally closest to the operator using the delivery device. The proximal and distal ends of a delivery device can also be referred to as the introduction end of the delivery device and the operator end of the delivery device. The operator end of the delivery device is that portion of the device that is intended to remain outside of a patient during a procedure. When referring to the prosthesis itself relative to the delivery device, the proximal end of the prosthesis is that part of the prosthesis nearest the delivery end of the delivery device and the distal end of the prosthesis is that end that is closest to the operator end of the delivery device. When referring to the prosthesis relative to placement in the human body, the ends of the various devices and parts of devices may be referred to as the inflow end (that end that receives fluid first, and the outflow end (that end from which the fluid exits).

Figure 1:
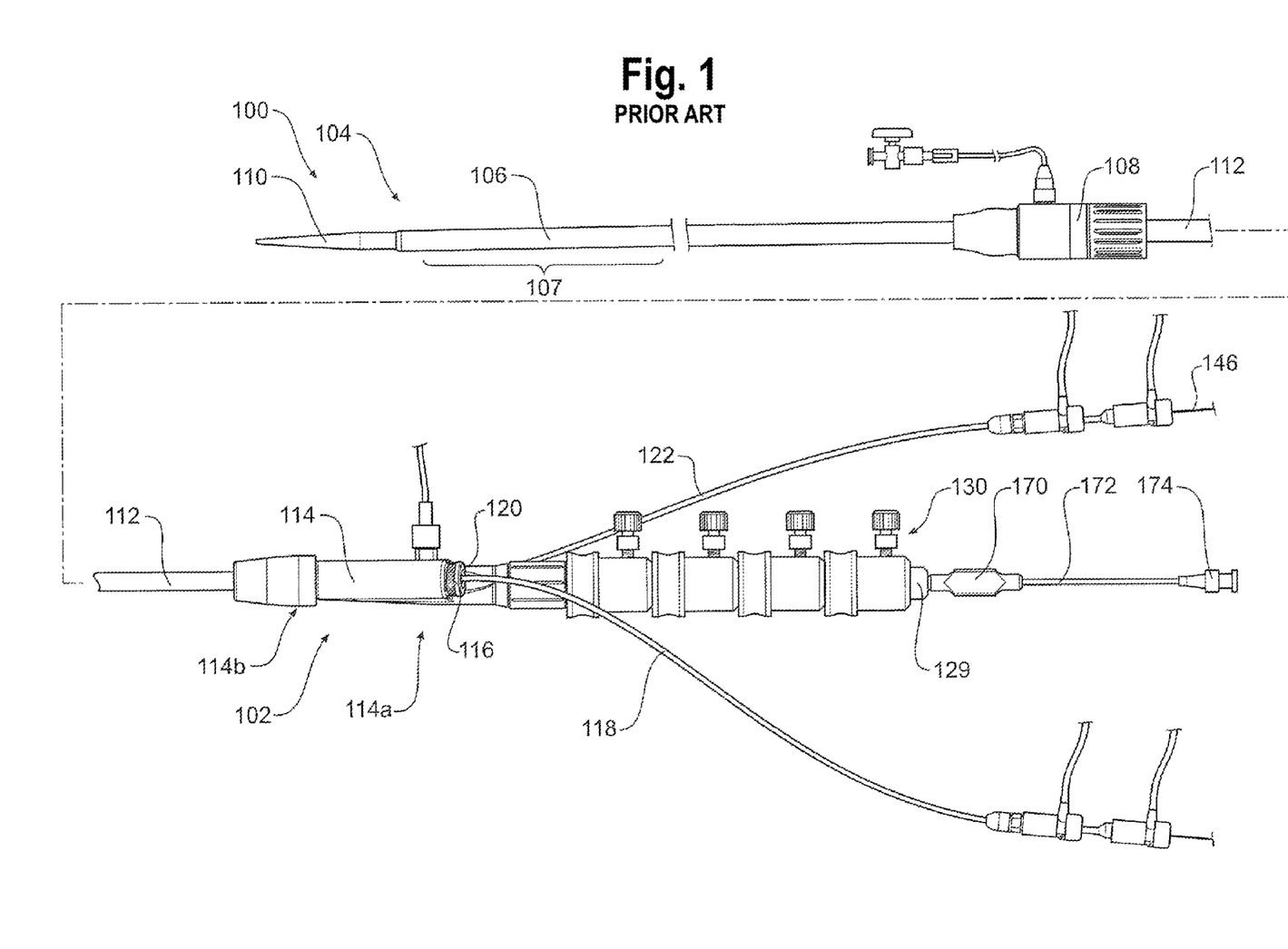
FIG. 1 shows a perspective view of a stent graft delivery device.
Figure 2:
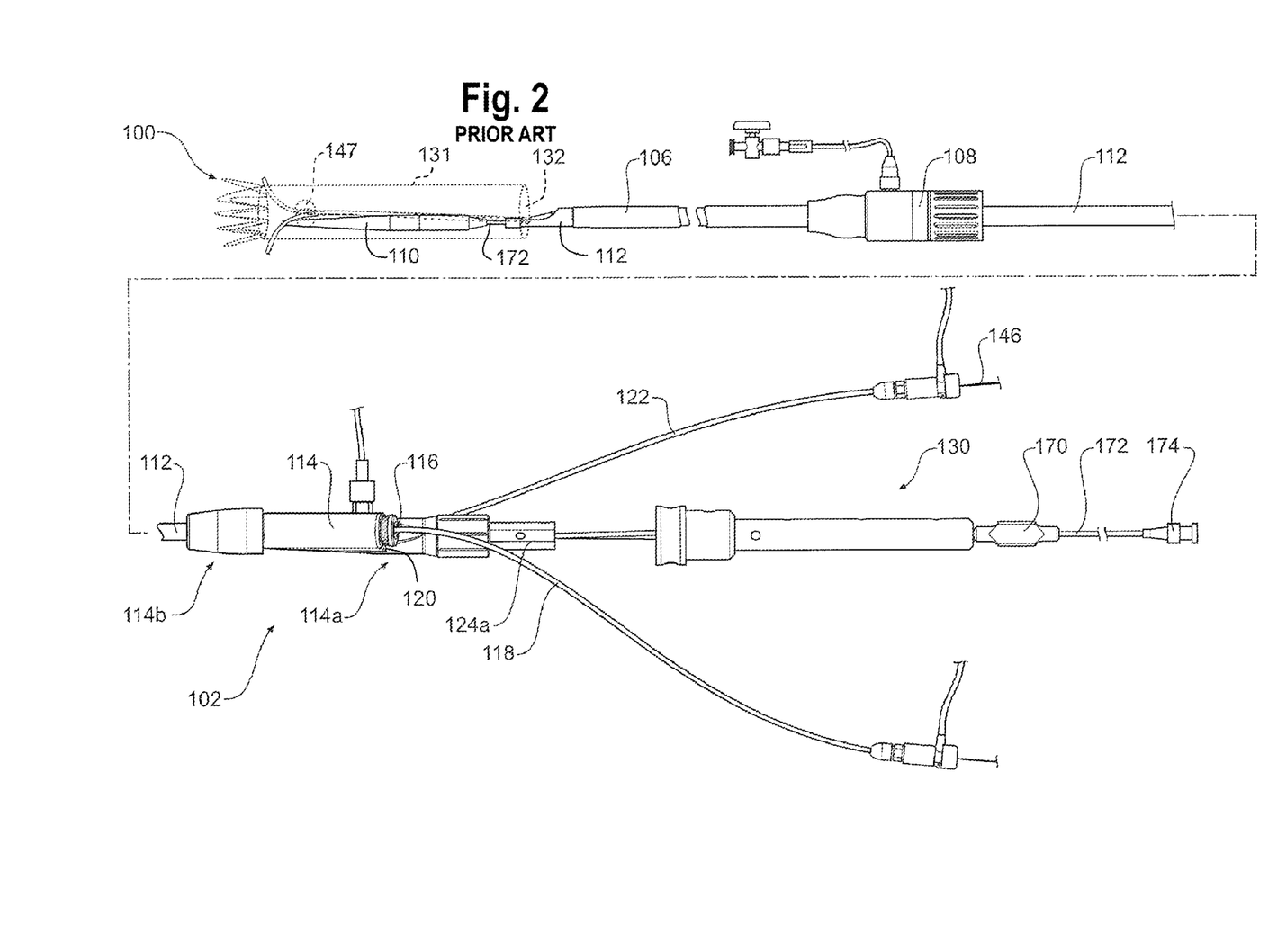
FIG. 2 shows a perspective view of the stent graft delivery device shown in FIG. 1 after the introducer sheath has been distally retracted and the stent graft has been deployed.
Figure 3:
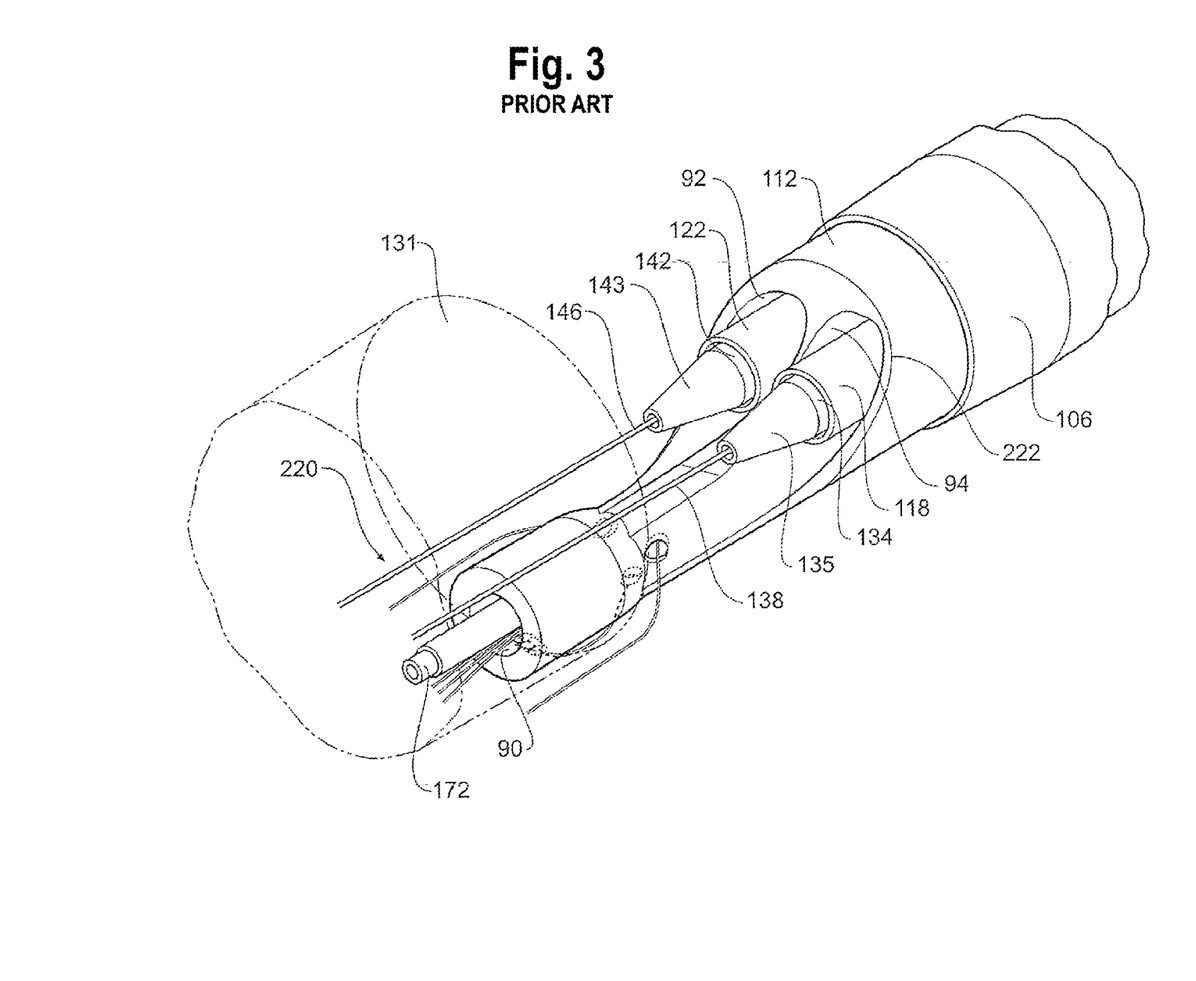
FIG. 3 shows a perspective view of the pusher catheter shown in FIG. 3.

FIG. 1 shows a perspective view of a stent graft delivery device. FIG. 2 shows a perspective view of the stent graft delivery device shown in FIG. 1 after the introducer sheath has been distally retracted and the stent graft has been deployed. FIG. 3 shows a perspective view of the pusher catheter shown in FIG. 3.

The delivery device 100 comprises a handle and manifold assembly 102 and introduction portion 104 intended to be deployed into a patient by the known Seldinger method.

More specifically the introducer section 104 includes a sheath 106 extending from a sheath hub 108 to a nose cone dilator 110. A stent graft 131 is retained within the outer sheath 106 in the region 107 just distal of the nose cone dilator 110 during insertion into the intended vessel, duct, or lumen.

The introducer portion 104 of the stent graft delivery device 100 has the nose cone dilator 110. The nose cone dilator 110 is elongated and include a tapered proximal end 109 for accessing and dilating a vascular lumen over a wire guide (not shown in FIGS. 1-3). The nose cone dilator 110 has a distal end and a distally facing capsule 213 on the distal end 211 of the nose cone dilator 110. A wire guide (not shown in FIGS. 1-3) may extend through a slidable guide wire catheter 172.

The nose cone dilator 110 may be disposed at the proximal end 173 of the guide wire catheter 172. The guide wire catheter 172 passes through and, at its proximal end, is fastened to a proximal end of the nose cone dilator 110. Distally, the guide wire catheter 172 passes through a handle assembly 130 of the delivery device and can terminate at syringe point 174. A pin vice arrangement 170 at the distal end of a distal handle portion 129 locks a movement of the guide wire catheter 172 with respect to the distal portion of the handle 129 and can be loosened to allow relative motion between these components.

A pusher catheter 112 extends from and may connect into a manifold 114. The manifold 114 has a proximal end 114b, in which the pusher catheter 112 is affixed, and a distal end 114a with two access ports 116, 120.

As shown in FIG. 2, the introducer sheath 106 may be retracted distally to expose the stent graft 131 during deployment when the deployment device is in a selected position within the vasculature of a patient. After the stent graft 131 has been partially or fully deployed, the guide wire catheter 172 (and the attached nose cone dilator 110) may be distally retracted. As a result, the nose cone dilator 110 may lie in a lumen 132 in the stent graft 131. As shown in FIG. 2, the nose cone dilator 110 may partially obstruct a fenestration 147 in the stent graft 131.

As shown in FIG. 3, the pusher catheter 112 has three longitudinally extending lumens 90 and 94. A first lumen is the guide wire lumen 90, which is off-set from the center of the pusher catheter to allow for two auxiliary lumens 92 and 94. The guide wire lumen 90 is configured to receive the guide wire catheter 172. The auxiliary lumens 92 and 94 are configured to receive auxiliary catheters 118 and 122, each of which has a dilator 143 or 135, respectively. The auxiliary catheters 118 and 122 may be configured to receive one or more auxiliary guide wires 146.

FIGS. 4-13 show an embodiment of a novel delivery system 200 designed to deploy a stent graft 231 in a body vessel, duct, or lumen. A prosthesis (in this case stent graft 231) may be deployed into a vessel, duct, or lumen using a variety of techniques. In one example, a guide wire may be inserted into the vessel with an introducer needle using, for example, the well-known percutaneous vascular access Seldinger technique. The delivery system 200 may be introduced over the guide wire to the deployment site.

An introducer sheath 206 may compress a stent graft 231 into the delivery system 200 so that the stent graft 231 may be delivered in a diameter-reduced configuration to a target site in the body. The stent graft 231 may be composed of a tubular body of a biocompatible graft material such as Dacron, expanded PTFE or Thoralon, a polyurethane material. The stent graft 231 may be supported by one or more self-expanding stents 300. A proximally extending exposed stent 237 may assist with providing infra-renal fixation of the deployed stent graft 231. The stent graft 231 may have one or more fenestrations 247 that are provided to give access to the renal arteries (not shown), or any other vessel. Diameter reducing ties 302 can be used to hold the stent graft in a diameter reduced condition. The tubular stent graft 131 of a biocompatible material may have one or more fenestrations 147 which are provided to give access to the renal arteries (not shown).

In general, the basic functionality of the delivery system shown in FIGS. 4-11 is similar to the prior art delivery system shown in FIGS. 1-3 and described above, with the exception of the design, function, and operation of a novel pusher catheter 212.

Figure 4:
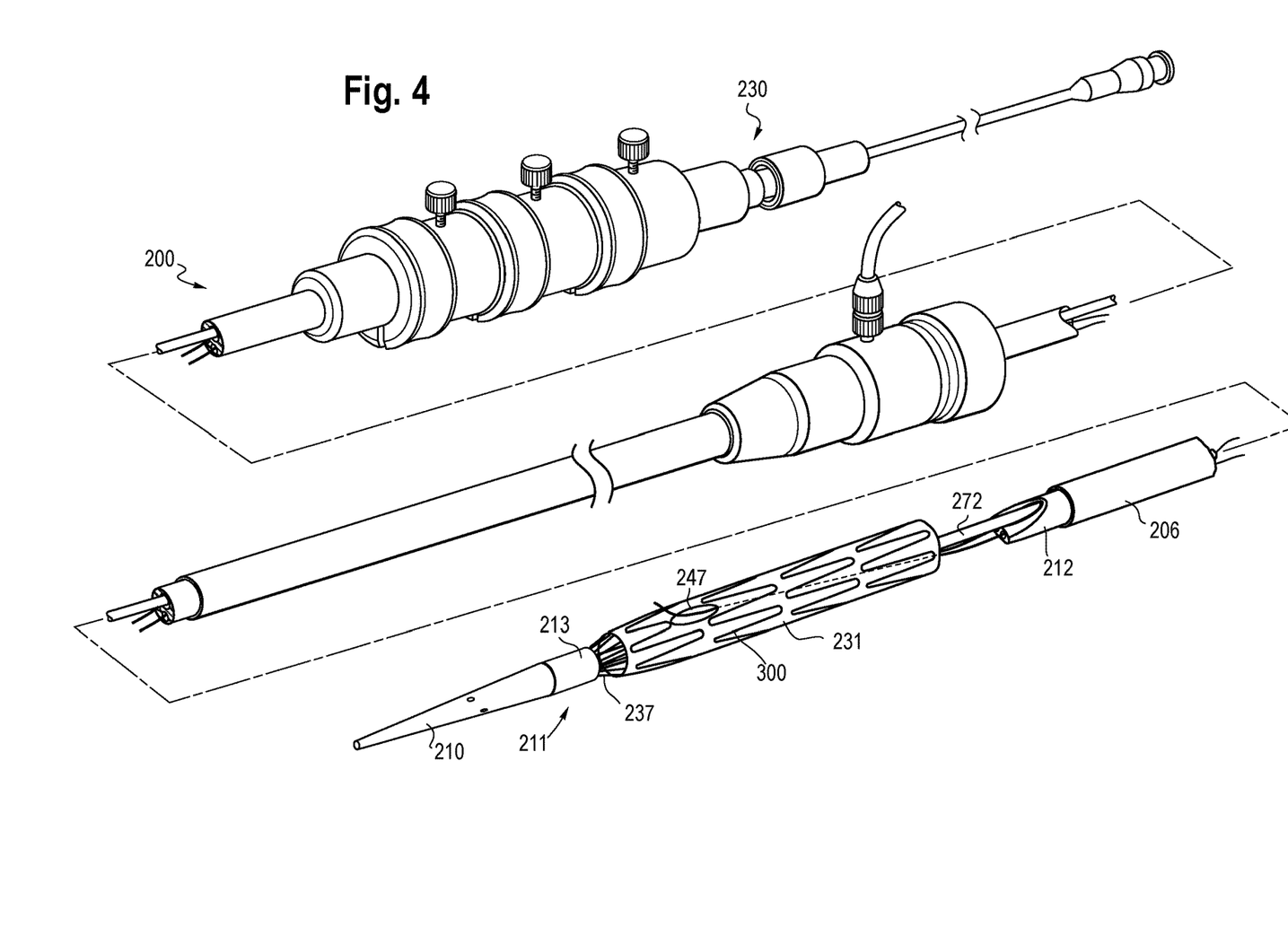
FIG. 4 shows an embodiment of a pre-loaded stent graft delivery system according to the present invention after an introducer sheath has been withdrawn.

As shown in FIG. 4, in one example a stent graft delivery device 200 includes a handle assembly 230, a nose cone dilator 210, a guide wire catheter 272 extending from the handle assembly 230 to and through the nose cone dilator 210, a pusher catheter 212 extending proximally from the handle assembly 230, and the stent graft 231.

In one example (not shown), the stent graft 231 may be attached to the pusher catheter 212 while in the delivery configuration. For example, there might be an attachment between the distal end of the stent graft 231 and the most proximal end of the pusher catheter 212 while the stent graft delivery device 200 is in a delivery configuration. The attachment between the stent graft 231 and the pusher catheter 212 may be on the opposite side of the pusher catheter so that it does not interfere with the guide wire catheter 272.

Upon removal of the attachment between the distal end of the stent graft 231 and the proximal pusher catheter 212, extra care will have to be taken because the main delivery wire will not protect the tip of the pusher catheter 212. The tip of the pusher catheter 212 may be protected by any preloaded wires, catheters, or sheaths while they are in place. An additional lumen for an additional wire may be provided to protect the pusher tip.

Figures 5, 6:
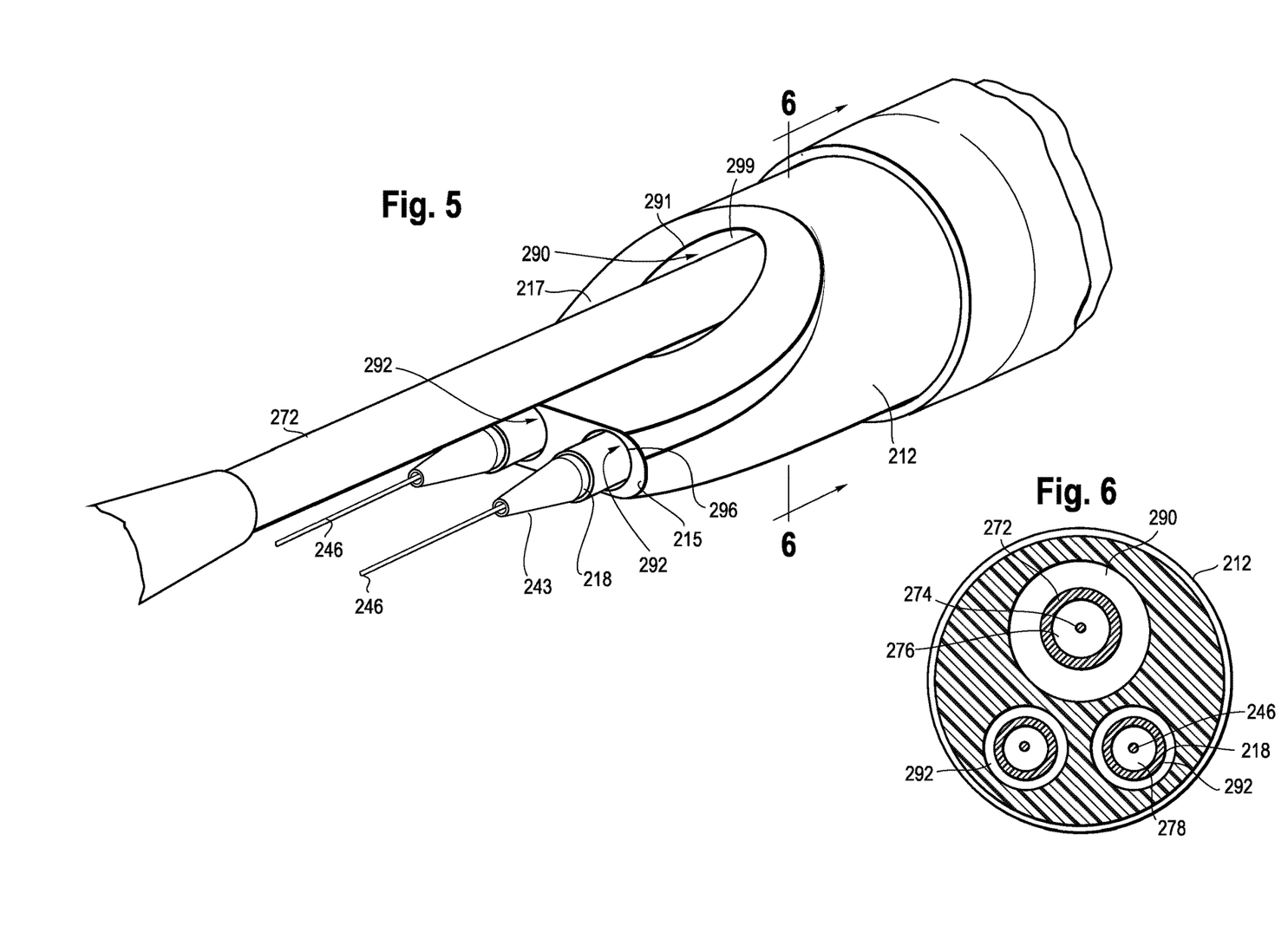
FIG. 5 shows a detailed view of the pusher catheter shown in FIG. 4.
FIG. 6 shows a latitudinal cross-sectional view of the pusher catheter shown in FIG. 5.

FIG. 5 shows a detailed view of the pusher catheter shown in FIG. 4. The novel pusher catheter 212 is elongate and flexible and has a most proximal end 215. The novel pusher catheter 212 may have a forward taper 217 near the most proximal end 215. The forward taper extends from one location on the outer cylindrical surface of the pusher catheter 212 toward a location on the opposite side of the pusher catheter 212. The forward taper 217 may be any suitable length and degree of slope. It may be steep or gradual. It may be a uniform taper or have a varying slope.

At the proximal end 215 of the pusher catheter 212, the taper terminates in an end face 219. The end face extends transverse to the longitudinal direction of the pusher catheter 212 and also transverse to the forward taper 217. The end face 219 may have rounded edges or have a curved surface for ensuring an atraumatic introduction.

The novel pusher catheter 212 has at least two lumens extending along its length. In one example, novel pusher catheter 212 has a guide wire lumen 290 that extends from the handle assembly 230 and terminates before the most proximal end 215 of the novel pusher catheter 212 within the taper 217 in a catheter lumen opening 291 distal to the most proximal end 215 of the novel pusher catheter 212.

As shown in FIGS. 4-13, the center of the guide wire lumen opening 291 may be distal to centers of one or more auxiliary lumen openings 296 (described below). In one example, the center of the guide wire lumen opening 291 is approximately 10-50 mm distal to the most proximal end 215 of the novel pusher catheter 212. The guide wire lumen opening 291 may be any suitable shape. In one example, the guide wire lumen opening 291 is generally oval shaped, due to the angled taper 217 intersecting a circular guide wire lumen 290. In one example, the guide wire lumen opening 291 may be approximately 2 mm wide.

The guide wire lumen 290 is configured to receive a guide wire catheter 272, which may be configured to receive a guide wire 274. The guide wire catheter 272 may be able to move longitudinally and rotationally with respect to the guide wire lumen 290.

The novel pusher catheter 212 may also have and one or more auxiliary lumens 292. As shown in FIGS. 4-13, in one example there may be two auxiliary lumens 292. The auxiliary lumens 292 may extend along the length of the novel pusher catheter 212 from the handle assembly 230 and terminate near the most proximal end 215 of the novel pusher catheter 212 in the end face 219.

The novel pusher catheter 212 may have one or more auxiliary lumen openings 296 in the end face 219. The auxiliary lumen openings 296 may be any suitable shape. In one example, the auxiliary lumen openings 296 is a generally circular shape, for example, determined by the end face 219 cutting across circular auxiliary lumens 292 at a right angle. Alternatively, where the end face 219 is rounded to at an oblique angle relative to the longitudinal direction, the auxiliary openings 296 may have an oval shape. In one example, the auxiliary lumen openings 296 may be approximately 2 mm wide. The auxiliary lumens may be arranged side-by-side at an equal distance from the guide wire opening 290.

Each of the auxiliary lumens 292 is configured to receive an auxiliary catheter 218, which may be configured to receive one or more auxiliary guide wires 246. The auxiliary catheter 218 may have an auxiliary dilator 243 disposed at its proximal end.

FIG. 6 shows a latitudinal cross-sectional view of the pusher catheter shown in FIG. 5. The novel pusher catheter 212 of FIG. 6 has three lumens: the guide wire lumen 290 and two auxiliary lumens 292. A guide wire catheter 272 may be disposed in the guide wire lumen 290. The guide wire 274 may extend through a lumen 276 in the guide wire catheter 272. Similarly, an auxiliary catheter 218 is disposed in one or both of the auxiliary lumens 292. An auxiliary guide wire 246 may extend through a lumen 278 in the auxiliary catheter 218.

Figure 7:
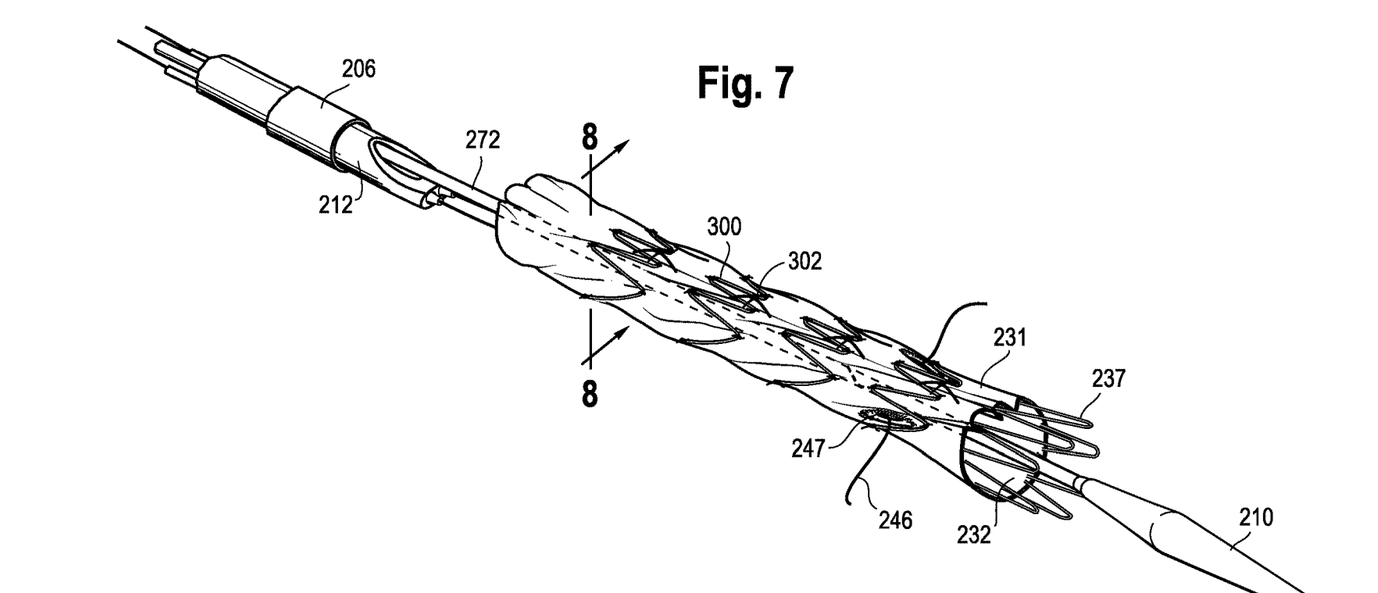
FIG. 7 shows the delivery system of FIG. 4 after the stent graft has been partially deployed.
Figure 8:
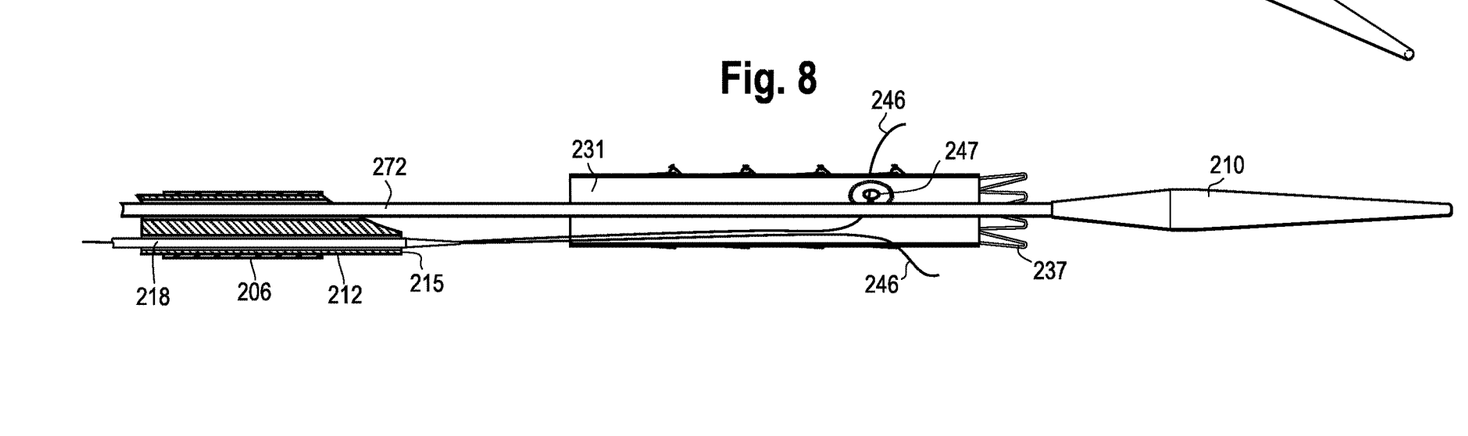
FIG. 8 shows a longitudinal cross-sectional view of the embodiment shown in FIG. 7.

After the delivery system 200 has been delivered to the target site, the introducer sheath 206 may be retracted and expose a stent graft 231. FIG. 7 shows the delivery system of FIG. 4 after the stent graft has been partially deployed. FIG. 8 shows a longitudinal cross-sectional view of the embodiment shown in FIG. 7.

As shown in FIGS. 7 and 8, the guide wire catheter 272 may extend proximally out of the guide wire lumen 290 and through a lumen 232 in the stent graft 231. The nose cone dilator 210 may extends from the proximal end of the guide wire catheter 272.

The one or more auxiliary guide wires 246 extend proximally out of the auxiliary lumen 292 and through a portion of a lumen 232 in the stent graft 231. In one example, an auxiliary guide wire 246 may extend through a fenestration 247 in the stent graft 231. The auxiliary guide wire 246 can be manipulated to enter a renal artery (not shown in FIGS. 7 and 8), for instance, and remain there while the stent graft 231 is partially or fully released from the delivery device 200.

Figure 9:
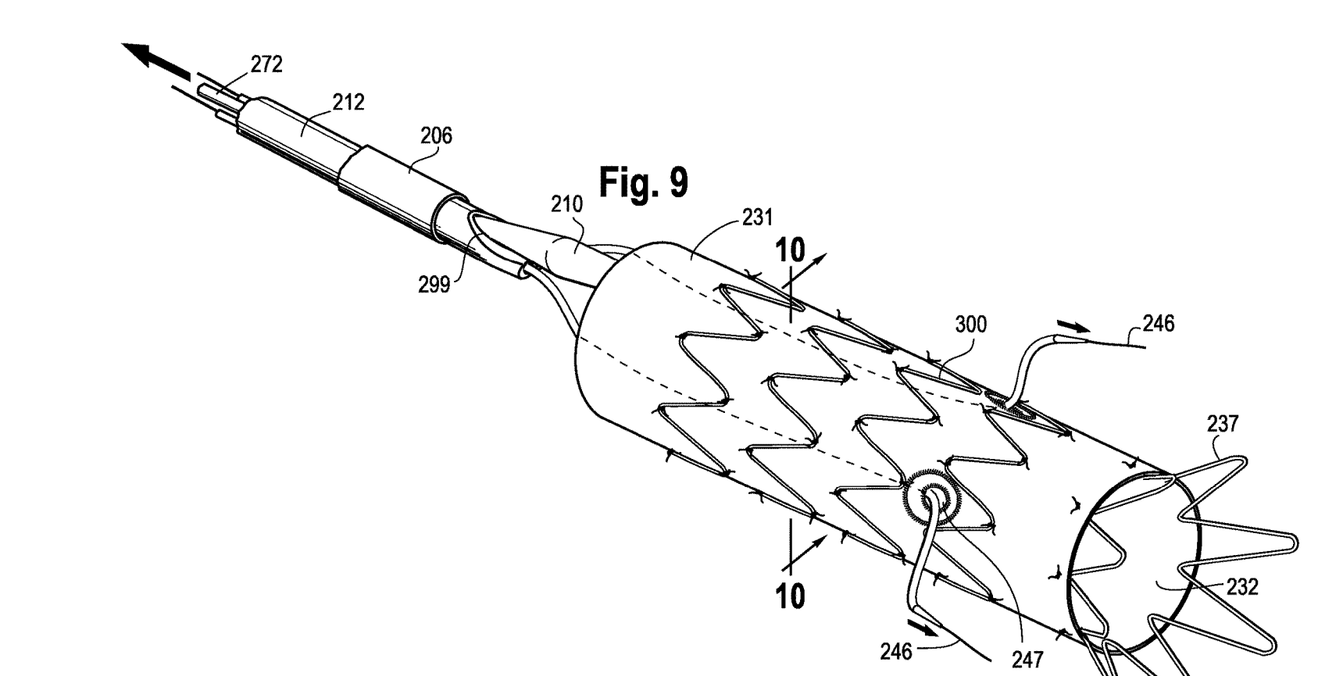
FIG. 9 shows the delivery system of FIG. 7 after the stent graft has been fully deployed and the nose cone dilator has been distally retracted.
Figure 10:
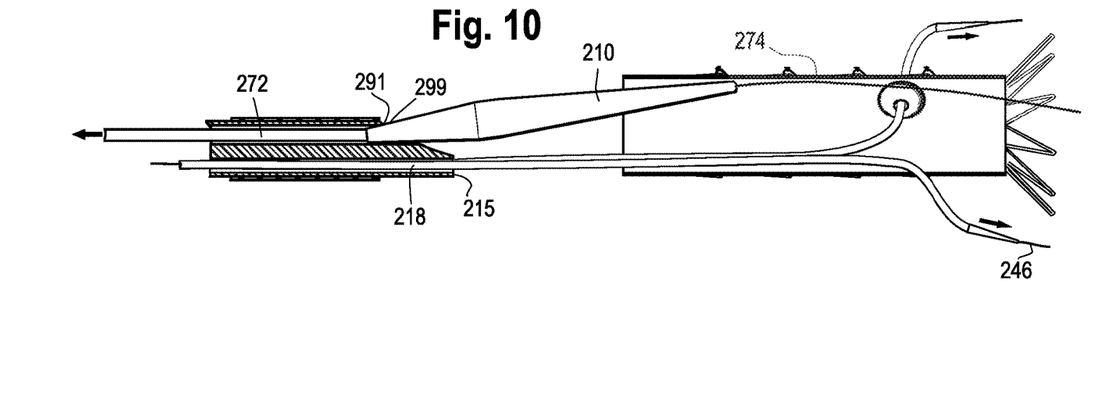
FIG. 10 shows a longitudinal cross-sectional view of the embodiment shown in FIG. 7.

FIG. 9 shows the delivery system of FIG. 7 after the stent graft has been fully deployed and the nose cone dilator has been distally retracted. FIG. 10 shows a longitudinal cross-sectional view of the embodiment shown in FIG. 10.

As shown in FIGS. 9 and 10, after the stent graft 231 has been fully deployed, the guide wire catheter 272 (and the nose cone dilator 210) may be distally retracted. In one example, the nose cone dilator 210 may partially be disposed in the guide wire lumen 290 in the pusher catheter 212.

As shown in FIG. 10, a recess 299 inside the guide wire lumen 290 adjacent to the guide wire lumen opening 292 may be configured to partially receive the nose cone dilator 210. Hence, the recess 299 has a shape that is configured to conform at least partially to the elongated nose cone dilator 210. In one example, the nose cone dilator 210 resides at least partially within the recess 299. The recess may be formed proximate to the angled taper 217 intersecting the circular guide wire lumen 290 where the guide wire lumen opening 291 is located. The proximal portion the guide wire lumen 290 may include an indent that conforms to at least a portion of the elongated nose cone dilator 210. The indent forming the recess 299 may be on a side of the guide wire lumen 290 adjacent to the auxiliary lumens 292.

The recess 299 may be located approximately 10-50 mm distal to the most proximal end 215 of the pusher catheter 212. In one example, the recess 299 may be near the guide wire lumen opening 291. The recess 299 may have any dimensions. In one example, the recess 299 may be approximately 6-7 mm.times.20-30 mm.

The recess may be formed by a gradual widening of the guide wire lumen 290 in the proximal direction toward the taper 217. For example, at least 10% or even at least 20% of the length of the nose cone dilator 210 may be disposed distally from the proximal end 215 of the pusher catheter 212 in this retracted position of the nose cone dilator 210.

As shown in FIGS. 9 and 10, one advantage over the delivery device shown in FIGS. 1-3 is that by allowing the nose cone dilator 210 to retract distal to the most proximal end 215 of the pusher catheter 212, the nose cone dilator 210 will be less likely to obstruct a fenestration 247 in the stent graft 231. In other words, because the nose cone dilator 210 can be retracted further distally than the most proximal end 215 of the pusher catheter, the nose cone dilator 210 does not extend as far into the lumen 232 of the stent graft 231. As a result, the nose cone dilator 210 is less likely to obstruct or cover access to a fenestration 247 in the stent graft 231. This advantage can especially be recognized during placement of bridging stents in one or more fenestrations 247.

Figure 11:
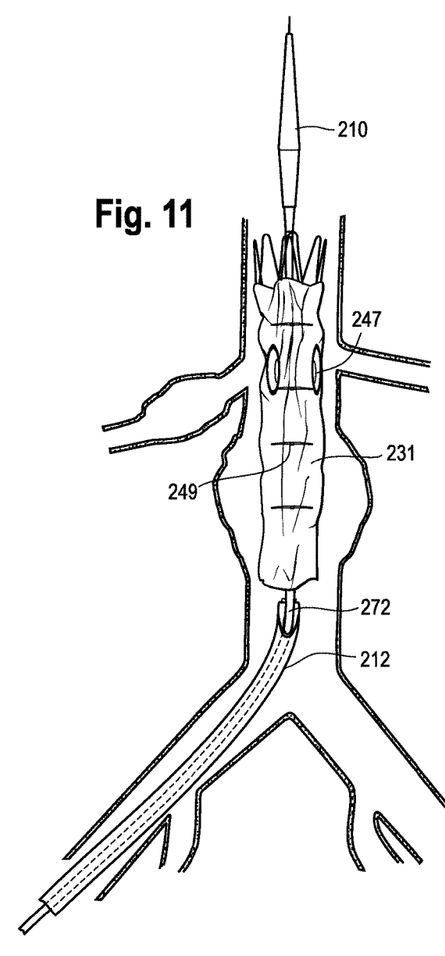
FIG. 11 shows an embodiment of a stent graft delivery system in a vessel.
Figure 12:
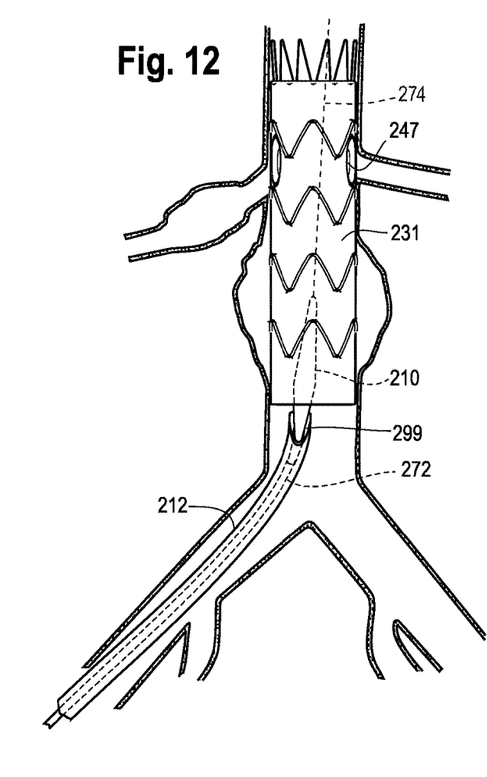
FIG. 12 shows the delivery system of FIG. 11 after the stent graft has been deployed and the nose cone dilator has been retracted.
Figure 13:
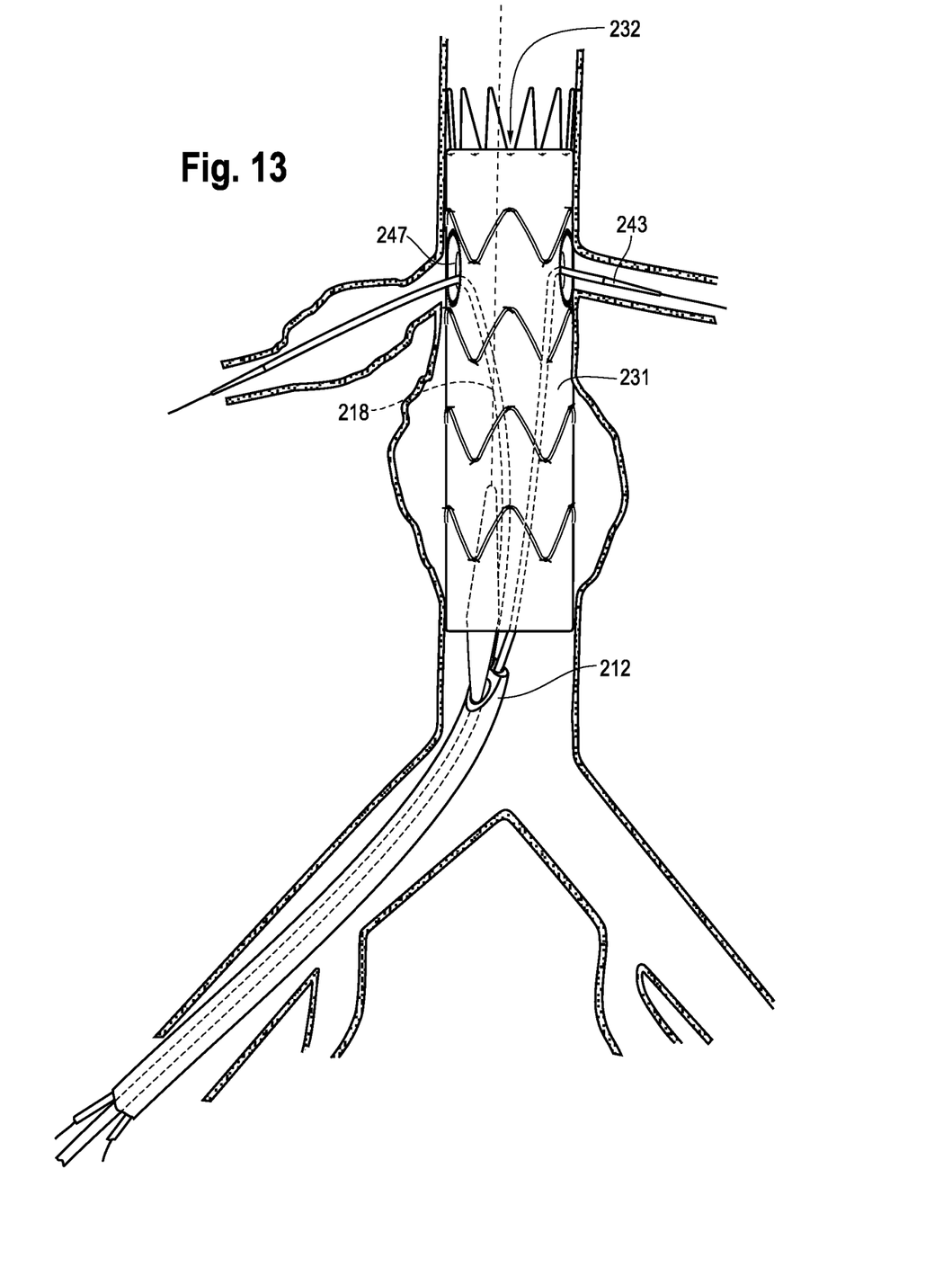
FIG. 13 shows the delivery system of FIG. 12 after the auxiliary catheters have cannulated the renal arteries.

FIGS. 11-13 show one example of a method for deploying a stent graft delivery device 200 using the novel pusher catheter 212 described above. In particular, FIG. 11 shows an embodiment of a stent graft delivery system in a vessel. FIG. 12 shows the delivery system of FIG. 11 after the stent graft has been deployed and the nose cone dilator has been retracted. FIG. 13 shows the delivery system of FIG. 12 after the auxiliary catheters have cannulated the renal arteries.

The delivery device 200 can be positioned into a vessel, duct, or lumen. As shown in FIG. 11, the delivery device may be delivered to the aorta. The stent graft 231 may be exposed after the introducer sheath 206 (not shown in FIGS. 11-13) is retracted distally. The stent graft 231 may be at least partially constrained with diameter reducing ties 249.

As shown in FIG. 12, the diameter reducing ties 249 may be released and the stent graft 231 may be allowed to expand within the vessel, duct, or lumen. After the stent graft 231 has been fully deployed, the guide wire catheter 272 and nose cone dilator 210 may be distally retracted. At least a portion of the nose cone dilator may be disposed in the recess 299 of the novel pusher catheter 212.

As shown in FIG. 13, after the guide wire catheter 272 and nose cone dilator 210 have been distally retracted, one or more auxiliary catheters 218 may be advanced through a lumen 232 in the stent graft 231 and/or through a fenestration 247.

While various embodiments of the invention have been described, the invention is not to be restricted except in light of the attached claims and their equivalents.

What is claimed is:

1. An endovascular prosthesis delivery system comprising:
   a slidable guide wire catheter having a proximal end;
   an elongate nose cone dilator secured to the proximal end of the guide wire catheter, the nose cone dilator having a shape;
   a pusher catheter having a most proximal end and at least two lumens therein, one of the lumens being a guide wire lumen and at least one of the lumens being an auxiliary lumen;
   wherein the guide wire catheter is at least partially disposed in the pusher catheter lumen;
   wherein the pusher catheter has a proximal taper adjacent a proximal most end of the pusher catheter;
   wherein the guide wire lumen proximally terminates in a guide wire lumen opening disposed in the taper, distal to the most proximal end of the pusher catheter; and
   wherein the at least one auxiliary lumen proximally terminates in an auxiliary lumen opening located closer to the most proximal end of the pusher catheter than the guide wire lumen opening.

2. The endovascular prosthesis delivery device of claim 1, wherein the guide wire lumen comprises a recess has a shape that at least partially conforms to the shape of the nose cone dilator.

3. The endovascular prosthesis delivery system of claim 2, wherein the nose cone dilator at least partially rests within the recess of the pusher catheter and at least partially extends distally of the most proximal end of the pusher catheter when in a retracted position.

4. The endovascular prosthesis delivery system of claim 1, wherein the nose cone dilator extends distally beyond the most proximal end of the pusher catheter when in a retracted position.

5. The endovascular prosthesis delivery system of claim 4, wherein the nose cone dilator has a retracted position, in which more than half of a length of the nose cone dilator is located distal from the most proximal end of the pusher catheter.

6. The endovascular prosthesis delivery system of claim 1, wherein the taper proximally ends at an end face of the pusher catheter, the end face extending transverse to a longitudinal direction of the pusher catheter.

7. The endovascular prosthesis delivery system of claim 6, wherein the at least one auxiliary lumen opening is located in the end face.

8. The endovascular prosthesis delivery system of claim 1, wherein the pusher catheter has three lumens.

9. The endovascular prosthesis delivery system of claim 1, wherein the nose cone dilator has a proximal taper and a distal taper.

10. The endovascular prosthesis delivery system of claim 9, wherein at least the distal taper of the nose cone dilator is disposed inside the guide wire lumen when the nose cone dilator is in a retracted position.

11. The endovascular prosthesis delivery system of claim 1, additionally comprising a stent graft having one or more fenestrations, the stent graft being connected to the proximal end of the pusher catheter when in a delivery configuration.

12. An endovascular prosthesis delivery system comprising:
   a guide wire catheter having a guide wire lumen therethrough;
   a nose cone dilator at a proximal end of the guide wire catheter, the nose cone dilator comprising a distal end and a distally facing capsule on the distal end of the nose cone dilator; and
   a pusher catheter having a most proximal end, the pusher catheter comprising a guide wire lumen configured to receive the guide wire catheter therethrough and at least one longitudinal auxiliary lumens configured to receive an auxiliary catheter, the guide wire catheter extending through the guide wire lumen and the guide wire catheter able to move longitudinally and rotationally with respect to the pusher catheter, the pusher catheter having a recess in the guide wire lumen adapted to a shape of the nose cone dilator to receive a portion of the nose cone dilator in a retracted position.

13. A catheter device comprising: a tubular body that extends from a proximal end to a distal end; an auxiliary lumen extending along the length of the tubular body that is configured to receive an auxiliary catheter, the auxiliary lumen having a proximal opening; and a guide wire lumen extending along the length of the tubular body, the guide wire lumen being configured to receive a guide wire catheter having a nose cone dilator at a proximal end of the guide wire catheter, wherein the nose cone dilator has a proximally facing taper and a distal portion; wherein the guide wire lumen has a proximal opening disposed distal to the proximal opening of the auxiliary lumen; and wherein the guide wire lumen opening is configured to receive the distal portion of the nose cone dilator.

14. The catheter device of claim 13, wherein the proximal end of the tubular body has a one-sided taper in an oblique direction relative to a longitudinal direction of the catheter device.

15. The catheter device of claim 14, wherein the taper proximally ends at an end face of the tubular body, the end face extending transverse to a longitudinal direction of the pusher catheter.

16. The catheter device of claim 15, wherein the auxiliary lumen proximally terminates in the end face.

17. The catheter device of claim 13, where in the nose cone distal portion comprises a distally facing taper and wherein the guide wire lumen opening is configured to receive at least the distally facing taper of the nose cone dilator.

18. The catheter device of claim 17, wherein the guide wire lumen opening is configured to receive the distal portion of the nose cone dilator to place more than half of a length of the nose cone dilator distal of the proximal end of the pusher catheter.

19. The catheter device of claim 17, wherein the guide wire lumen includes a recess with a shape adapted to the nose cone dilator for placing a distal portion of the nose cone dilator inside the guide wire lumen.

20. The catheter device of claim 13, wherein the guide wire lumen opening is between 10-50 mm distal to the proximal end of the catheter.

* * * * *